(12) United States Patent
Laurencin et al.

(10) Patent No.: US 6,689,166 B2
(45) Date of Patent: Feb. 10, 2004

(54) HYBRID NANOFIBRIL MATRICES FOR USE AS TISSUE ENGINEERING DEVICES

(75) Inventors: Cato T. Laurencin, Elkins Park, PA (US); Frank K. Ko, Philadelphia, PA (US)

(73) Assignee: Drexel University, Philadelphia, PA (US)

( * ) Notice: Subject to any disclaimer, the term of this patent is extended or adjusted under 35 U.S.C. 154(b) by 0 days.

(21) Appl. No.: 10/267,133

(22) Filed: Oct. 8, 2002

(65) Prior Publication Data

US 2003/0050711 A1 Mar. 13, 2003

Related U.S. Application Data

(63) Continuation of application No. 09/529,278, filed as application No. PCT/US98/21369 on Oct. 9, 1998, now abandoned.

(60) Provisional application No. 60/080,445, filed on Apr. 2, 1998.

(51) Int. Cl.[7] .................................................. A61F 2/02
(52) U.S. Cl. .................................. 623/11.11; 623/23.74
(58) Field of Search ........................... 623/11.1, 16.11, 623/23.56, 23.51, 23.72, 23.74; 428/36.3; 530/356

(56) References Cited

U.S. PATENT DOCUMENTS

| | | | |
|---|---|---|---|
| 4,970,298 A | 11/1990 | Silver et al. | 530/356 |
| 6,106,913 A | 8/2000 | Scardino et al. | 428/36.3 |

*Primary Examiner*—David J. Isabella
(74) *Attorney, Agent, or Firm*—Licata & Tyrrell P.C.

(57) ABSTRACT

Tissue engineering devices with enhanced cell adhesion, cell proliferation and directional growth are provided which are prepared from nonwoven nanofibril matrices.

2 Claims, 1 Drawing Sheet

HYBRID NANOFIBRIL MATRICES FOR USE AS TISSUE ENGINEERING DEVICES

INTRODUCTION

This application is a continuation of U.S. application Ser. No. 09/529,278, filed Jul. 18, 2000, now abandoned which was the National Stage of International Application No. PCT/US98/21369 filed Oct. 9, 1998. This application claims the benefit of U.S. Provisional Application No. 60/080,445, filed Apr. 2, 1998.

This invention was made in the course of research sponsored by the National Science Foundation. The U.S. Government may have certain rights in this invention.

FIELD OF THE INVENTION

It has now been found that the components in biocompatible scaffolds or matrices of nanometer diameter provide favorable environments for cell adhesion, cell proliferation and directional growth. Fibrous and fibrillar organic and inorganic biocompatible materials of nanometer diameter can be integrated into nonwoven three-dimensional matrices conducive for cell seeding and proliferation. These three-dimensional scaffolds or matrices can then be fabricated into appropriate shapes to simulate the hierarchical micro- and macro-geometry of tissues and/or organs to be repaired or replaced.

BACKGROUND OF THE INVENTION

The unique combination of light weight, flexibility, permeability, strength and toughness of linear, 2-dimensional and 3-dimensional textile structures renders them useful in a variety of ways beyond traditional apparel. Various fiber structures are disclosed by Ko, F. K. in *Textile Structural Composites*, Chou, T. W., and Ko, F. K., eds., Elsevier, 1989, and *Bull. Am. Cer. Soc. February* 1989. An important element dictating the physical characteristics of a textile structure and its usefulness in various applications is the fineness as determined by diameter and linear density of the fibers. In general the range of fiber fineness expressed in terms of fiber diameter has been well above 2 μM. Also important is the organization and orientation of these fibers.

Many of the applications for these structures including, but not limited to, medical devices and chemical separation and/or protection apparatus require broad ranges of fiber architecture, packing density, surface texture, porosity, total reactive surface areas and fiber tortuosity. Accordingly, it would be of great advantage in the art in many of these uses, if fibers of smaller diameter with greater strength could be prepared. For example, trauma, pathological degeneration, or congenital deformity of tissues can result in the need for surgical reconstruction or replacement. Reconstructive surgery is based upon the principle of replacing these types of defective tissues with viable, functioning alternatives. In skeletal applications, surgeons have historically used bone grafts. The two main types of bone grafts currently used are autografts and allografts. An autograft is a section of bone taken from the patient's own body, while an allograft is taken from a cadaver. This method of grafting provides the defect site with structural stability and natural osteogenic behavior. However, both types of grafts are limited by certain uncontrollable factors. For autografts, the key limitation is donor site morbidity where the remaining tissue at the harvest site is damaged by removal of the graft. Other considerations include the limited amount of bone available for harvesting, and unpredictable resorption characteristics of the graft. The main limitation of allografts has been the immunologic response to the foreign tissue of the graft. The tissue is often rejected by the body and is subject to the inflammatory response. Allografts are also capable of transmitting disease. Although a thorough screening process eliminates most of the disease carrying tissue, this method is not 100% effective.

Conventional orthopedic implants such as screws, plates, pins and rods serve as loadbearing replacements for damaged bone and are usually composed of a metal or alloy. Although these implants are capable of providing rigid fixation and stabilization of the bone, they cause improper bone remodeling of the implant site due to the large difference in the modulus between bone and metal.

These limitations have initiated the search for a dependable synthetic bone graft substitute. However, in order for an implant to be used as a replacement for bone, it must be capable of both osteointegration and osteoconduction. Osteointegration refers to direct chemical bonding of a biomaterial to the surface of bone without an intervening layer of fibrous tissue. This bonding is referred to as the implant-bone interface. A primary problem with skeletal implants is mobility. Motion of the implant not only limits its function, but also predisposes the implant site to infection and bone resorption. With a strong implant-bone interface, however, mobility is eliminated, thus allowing for proper healing to occur. Osteoconduction refers to the ability of a biomaterial to sustain cell growth and proliferation over its surface while maintaining the cellular phenotype. For osteoblasts, the phenotype includes mineralization, collagen production, and protein synthesis. Normal osteoblast function is particularly important for porous implants that require bone ingrowth for proper strength and adequate surface area for bone bonding. In addition, implants should be both biocompatible and biodegradable.

Three-dimensional polymer matrix systems have shown considerable promise for tissue regeneration because of their increased surface area for cell growth, pathways for cellular migration and channels for transport of nutrients and effector molecules to cells (Eggli et al. *Clin. Orthop.* 1987 232:127–138; Allcock et al. *Macromolecules* 1977 10:824–830). Porous, three-dimensional matrices comprising biodegradable, biocompatible polymers or copolymers such as poly(lactic acid-glycolic acid), referred to herein as PLAGA, and its homopolymer derivatives, PLA and PGA, have been demonstrated to be useful in skeletal repair and regeneration (Coombes, A. D. and Heckman, J. D. *Biomaterials* 1992 13:217–224; Mikos et al. *Polymer* 1994 35:1068–1077; Robinson et al. *Otolaryngol. Head and Neck Surg.* 1995 112:707–713; Thomson et al. *J. Biomater. Sci. Polymer Edn.* 1995 7:23–38; Devin et al. *J. Biomateri. Sci. Polymer Edn.* 1996 7:661–669). Pores of these structures are believed to aid in the polymer resorption-graft incorporation cycle by increasing pathways through which cells can migrate, increasing the surface area for cell attachment, providing pathways by which nutrients may reach the cells, and increasing the polymer surface exposed to the degradation medium (Attawia et al. *Biochem. and Biophys. Res. Commun.* 1995 213(2):639–644). Accordingly, much of the research concerning production of polymeric matrices for tissue engineering has focused upon formation of matrices of adequate pore size which maintain the compressive strength required for a bone replacement device. Due to the size of osteoblasts, studies have established 100 μM as the minimum pore diameter required for the successful ingrowth of bone cells to these scaffolds (Friedlander, G. *Bone and Cartilage Allografts*, AAOS, Park Ridge, Ill., 1991).

It has now been found, however, that tissue engineered devices with enhanced properties of cell adhesion, cell proliferation and directional growth can be prepared from matrices comprising biocompatible fibers of a diameter which is an order of magnitude smaller than the cells. Accordingly, the present invention relates to fibers of nanometer diameter, referred to herein as nanofibrils, with adequate strength for use in textile processing processes and methods of producing these nanofibrils. Tissue engineering devices are also provided which are prepared from scaffolds or matrices comprising nonwoven nanofibrils.

SUMMARY OF THE INVENTION

An object of the present invention is to provide fibers of nanometer diameter and adequate strength to be useful in textile processing processes. These fibers of the present invention are referred to herein as "nanofibrils."

Another object of the present invention is to provide a method of making nanofibrils for use in nanofibril matrices.

Yet another object of the present invention is to provide a tissue engineered device with enhanced properties of cell adhesion, cell proliferation and directional growth which comprises a nonwoven nanofibril matrix.

DETAILED DESCRIPTION OF THE INVENTION

Figure 1:
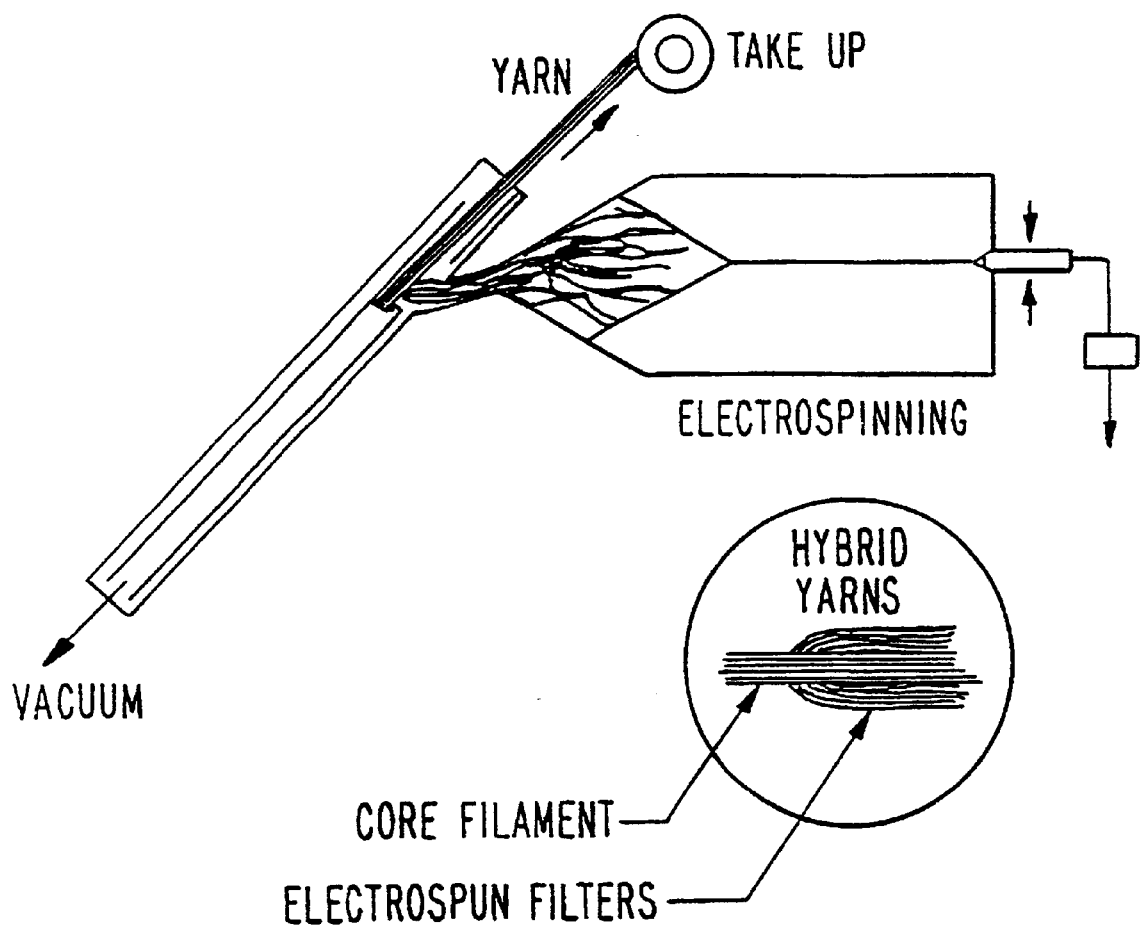
FIG. 1 shows a schematic diagram of a hybrid yarn spinning system which is used in an Air Vortex Spinning (AVS) process to produce matrices comprising nanofibrils of the present invention and stronger fibers or filaments.

As a result of advances in biotechnology and the development of new biomaterials in recent years, tissue engineering is becoming a method of choice for the development of implants in surgery. However, to create three-dimensional scaffolds conducive for cell deposition and cell proliferation, the dynamic interaction of cell and matrix substances must be understood. There is a large family of fiber architectures available for surgical implants with varying fiber tortuosity and fabric porosity.

In general textile fibers have a diameter ranging from 1 $\mu$M to 10 $\mu$M, and a denier ranging from $10^{-3}$ to 10. While electrospun fibers of lower diameters and deniers have been produced, a current limitation of fiber architectures is the lack of sufficient strength for fibrils of diameters of less than 2 $\mu$M to withstand the rigors of textile processing. The fineness of fibers having diameters of less than 2 $\mu$M also makes them prone to stick to surfaces during processing.

In the present invention, a method is provided for the production of fibers of nanometer diameter, referred to herein as nanofibrils, having a diameter ranging from approximately 4 Å to 100 nm, and a nanodenier of about $10^{-9}$. The nanofibrils of the present invention are made sufficiently strong to permit their use in textile processing processes by combining the fibrils with stronger fibers or filaments. Problems caused by surface contact and sticking is minimized via use of pneumatic (air) or fluid based processing of the fibrils. These nanofibrils, in combination with carrier or strengthening fibers or filaments can be converted directly into nonwoven fibrous assemblies or converted into linear assemblies, referred to as yarns, before weaving, braiding or knitting into 2-dimensional and 3-dimensional fabrics. In a preferred embodiment, an electrospinning process is used to produce the desired nanofibrils. Alternatively, nanofibrils of the present invention can be used alone to form fibrous networks held together by interfiber adhesion.

In one embodiment, an Air Vortex Spinning process is used to produce matrices comprising nanofibrils of the present invention and stronger fibers or filaments. In this process, electrospun fiber is fed into an air vortex spinning apparatus to form a linear fibrous assembly. This process makes use of an air stream in a confined cavity to produce a vortex of air which provides a gentle means for converting a mixture of nanofibrils fed directly or indirectly from an electrospinning unit and a fiber mass or filament of higher strength into an integral assembly with proper level of orientation.

Examples of textile fabric architecture that can be produced via this process include, but are not limited to, biaxial woven, high modulus woven, multilayer woven, triaxial woven, tubular braid, tubular braid in warp, flat braid, flat braid laid in warp, weft knit, weft knit laid in weft, weft knit laid in warp, weft knit laid in weft laid in warp, square braid, square braid laid in warp, 3-dimensional braid, 3-dimensional braid laid in warp, warp knit, warp knit laid in warp, weft inserted warp knit, weft inserted warp knit laid in warp, fiber mat, stitch bonded laid in warp, biaxial bonded and xyslaid in system.

In another embodiment, matrices comprising nanofibrils of the present invention are prepared using an extension of the traditional 2-dimensional braiding technology in which fabric is constructed by the intertwining or orthogonal interlacing of yarns to form an integral structure through position displacement. In this embodiment, a wide range of 3-dimensional shapes are fabricated in a circular or rectangular loom. The resulting linear fiber assembly or yarn is a hybrid of nano- and micro-fibers with a strong core filament which combines the two texture surfaces and strengths into one assembly.

As will be obvious to those of skill in the art upon this disclosure, however by properly controlling the processing conditions, a wide variety of matrices comprising the nanofibrils with differing surfaces, microporosity and strength can be tailor made for their particular use.

Further, it has now been demonstrated that the fibrils of nanometer diameter of the present invention in various selected architectures enhance interaction of the scaffold or matrix with cells such as osteoblasts. By "enhanced" it is meant that the scaffold or matrix is prepared from fibrils of nanometer diameter in a configuration or architecture which optimizes interactions between the scaffold or matrix and cells which are required for the intended purpose of the matrix. Examples of nanofibril materials which can be used in this embodiment the present invention include, but are not limited to, non-degradable polymers such as polyethylenes and polyurethanes and degradable polymers such as poly (lactic acid-glycolic acid), poly(lactic acid), poly(glycolic acid), poly(glaxanone), poly(orthoesters), poly(pyrolicacid) and poly(phosphazenes). Other components which can be incorporated into the matrices include, but are not limited to, calcium phosphate based ceramics such as hydroxyapatite and tricalcium phosphate. By "nanometer diameter" it is meant to include fibrils ranging in diameter from approximately 1 nanometer ($10^{-9}$ meters) to approximately 10,000 nanometers. More preferably, the fibrils range in diameter from 3 to 300 nanometers.

Experiments have now been conducted which demonstrate that cell growth patterns are related to the relative dimensions of the components of a matrix and the cells. In these experiments, four matrices were fabricated for cell culture including: a matrix comprising sintered 150–300 μM PLAGA spheres; a matrix comprising unidirectional bundles of 20 μM filaments; a matrix comprising a three-dimensional braided structure consisting of 20 bundles of 20 μM filaments; and a nonwoven matrix consisting of nanofibrils. Cells were seeded on the ultraviolet sterilized PLAGA matrices at a density of 100,000 cells/cm$^2$. The osteoblasts were cultured on the matrices for durations ranging from one day to twenty-one days and prepared according to established procedures by fixation in glutaraldehyde and dehydration through a series of ethanol dilutions.

Scanning electron microscopy (SEM) photographs of the osteoblasts cultured on these matrices were taken. In matrices with larger spheres such as the matrix of sintered 150–300 μM PLAGA spheres, wherein the cells are more than 10,000 times smaller than the spheres, the cells tended to spread over the surface before connecting to the adjacent spheres to eventually form an interconnected network. The cell matrix reaction was similar in matrices of 20 μM filaments in unidirectional bundles and the three-dimensional braided structure wherein the cell are about the same order of magnitude in dimension. In these matrices, the cells tended to slide off the matrix at the moment of seeding. Those cells remaining on the surface of the substrates tended to grow around the filaments and braided structure onto the adjacent filaments along the length.

In contrast, the nanofibril nonwoven matrix, wherein the cells are more than an order of magnitude larger than the individual fibrils, showed intensive cell deposition. In this matrix, extensive cell spreading was observed along the length of the fibrils and through the thickness of the fibril assembly. Results from these experiments thus indicate that cell affinity and cell growth patterns in tissue engineering devices can be enhanced using matrices comprising biocompatible components of nanometer diameter.

Accordingly, the present invention also provides matrices comprising biocompatible nonwoven nanofibrils which are useful in tissue engineering devices such as implants. By "implants" it is meant to include, but is not limited to, orthopedic implants such as bone, cartilage, ligaments, and tendons, and scaffolds for muscle, blood vessels and cardiac tissue. Such implants can be in the form of universal scaffolds which are delivered as croutons in sterilized packages which include, but are not limited to graft materials for bones and osteochondral grafts for cartilage, living scaffolds delivered in a bioreactor which contains the cell matrix system, and custom scaffolds to be used in conjunction with novel cellular products and growth factors.

The following nonlimiting examples are provided to further illustrate the present invention.

EXAMPLES

Example 1

Cell Cultures

Osteoblasts used in these experiments were isolated from neonatal rat calvaria and grown to confluence in Ham's F-12 medium (GIBCO BRL Life Technologies, Gaithersburg, Md.). These osteoblasts were supplemented with 12% fetal bovine serum (Sigma Chemical Company, St. Louis, Mo.) prior to seeding.

Example 2

Scanning Electron Microscopy Pictures

Scanning electron microscopy (SEM) pictures were taken for the cell-matrix systems which were prepared in 25%, 50%, 75% and 100% Freon 113 dilutions. The SEM samples were sputter coated with gold using a Denton Desk-1 Sputter Coater. An Amray 3000 SEM using an accelerating voltage of 20 kV was employed to take the SEM photographs.

Example 3

Preparation of Matrices

Sintered Microsphere Matrix

Biodegradable polymeric microspheres were placed in a Teflon-lined dish. The microspheres were then heated above their glass transition temperature for a predetermined period of time to obtain a 3-dimensional porous matrix.

Unidirectional Matrix

Three hundred individual biodegradable polymeric fibers with the desired length were bundled together and taped at the ends to obtain a fibrous matrix.

Three-Dimensional Braided Matrix

Forty-eight yarn bundles of biodegradable fibers were braided in a braiding loom to create a fully integrated, interconnected three dimensional fibrous network. The three-dimensional scaffold can be used as fabricated for cell seeding or sintered before cell seeding and implantation.

Nanofiber Nonwoven Matrix

Biodegradable polymer solutions were splayed using an electrospinning method on a collecting screen to form a fibrous network held together by interfiber cohesion.

What is claimed is:

1. A tissue engineering device comprising a matrix of biocompatible nonwoven nanofibrils comprising a non-degradable polymer selected from the group consisting of polyethylenes and polyurethanes or a degradable polymer selected from the group consisting of poly(lactic acid-glycolic acid), poly(lactic acid, poly(glycolic acid), poly glaxanone), poly(orthoesters), poly(pyrolic acid) and poly (phosphazenes).

2. The tissue engineering device of claim 1 further comprising a calcium phosphate based ceramic material.

* * * * *